US011786671B2

(12) United States Patent
Fischer et al.

(10) Patent No.: US 11,786,671 B2
(45) Date of Patent: Oct. 17, 2023

(54) PROTECTIVE DEVICE FOR THE NEEDLE TUBE OF A SYRINGE

(71) Applicants: Stephan Fischer, Hiddenhausen (DE); Tobias Wilke, Ibbenbueren (DE); Bernd Mohr, Barnstedt (DE)

(72) Inventors: Stephan Fischer, Hiddenhausen (DE); Tobias Wilke, Ibbenbueren (DE); Bernd Mohr, Barnstedt (DE)

(73) Assignee: CA-DIGITAL GmbH, Hilden (DE)

( * ) Notice: Subject to any disclaimer, the term of this patent is extended or adjusted under 35 U.S.C. 154(b) by 0 days.

(21) Appl. No.: 17/566,799

(22) Filed: Dec. 31, 2021

(65) Prior Publication Data
US 2022/0193348 A1 Jun. 23, 2022

Related U.S. Application Data

(63) Continuation of application No. PCT/EP2019/079385, filed on Oct. 28, 2019.

(30) Foreign Application Priority Data

Jul. 15, 2019 (DE) .......................... 202019103876.4

(51) Int. Cl.
*A61M 5/32* (2006.01)

(52) U.S. Cl.
CPC ......... *A61M 5/3216* (2013.01); *A61M 5/3202* (2013.01); *A61M 2005/3217* (2013.01)

(58) Field of Classification Search
CPC .............. A61M 5/3202; A61M 5/3126; A61M 5/5086; A61M 2005/3217; A61M 2005/3279
See application file for complete search history.

(56) References Cited

U.S. PATENT DOCUMENTS

| 5,885,249 | A | * | 3/1999 | Irisawa | ............... | A61M 5/3216 604/263 |
| 8,801,672 | B2 | * | 8/2014 | Nagy | .................. | A61M 5/3216 604/192 |
| 2002/0193744 | A1 | * | 12/2002 | Alesi | ................... | A61M 5/3216 128/919 |
| 2009/0018510 | A1 | * | 1/2009 | Madin | ................. | A61M 5/3216 604/192 |

FOREIGN PATENT DOCUMENTS

| DE | 202018107052 | 2/2019 |
| WO | WO2009007718 A1 | 1/2009 |
| WO | WO2018172853 | 9/2018 |

* cited by examiner

*Primary Examiner* — Nathan R Price
*Assistant Examiner* — Justin L Zamory
(74) *Attorney, Agent, or Firm* — Von Rohrscheidt Patents

(57) ABSTRACT

A protective device for the needle tube of a syringe, including a housing which can be pivoted on a support base which has an open housing side in the pivot plane, so that the needle tube can be pivoted into the housing after being used for injection and wherein on the housing side, a retaining device is provided for the needle tube which has been pivoted inwards. The invention proposes that in addition to the connection of a film hinge in order to form a pivot axis, the support base and the pivotable housing are additionally connected together via a predetermined breaking point and wherein after being used for injection, the housing can be pivoted back over the destroyed predetermined breaking point.

17 Claims, 13 Drawing Sheets

PROTECTIVE DEVICE FOR THE NEEDLE TUBE OF A SYRINGE

RELATED APPLICATIONS

This application is a continuation of International Application PCT/EP2019/079385 filed on Oct. 28, 2019, claiming priority from German Patent Application DE 20 2019 103 876.4 filed on Jul. 15, 2019, both of which are incorporated in their entirety by this reference.

FIELD OF THE INVENTION

The invention relates to a protective device for the needle tube of a syringe

BACKGROUND OF THE INVENTION

It is known that the needle of a hypodermic syringe normally comprises a metal tube provided with a syringe and connected to a hollow support base and which is connected to the cylindrical body of a syringe. The present invention is concerned here with the problem of protecting the metal tube against needlestick, in this case in particular after a patient's body has been injected, in order to avoid injecting people who might come into contact with the needle following the treatment. If a second person is stabbed with the needle after it has been used on a first person, then this could lead to the transmission of diseases. Thus, a considerable risk is attached to the use of these needles, especially for those who normally work with them, i.e. in particular for hospital and clinic personnel. The disposal of used needles as waste also endangers those who handle the waste containers or who get close to these containers.

Because of these circumstances, it is particularly important for the needle tube to be protected after the injection in order thereby to prevent the possibility of the transmission of diseases.

In order to counter this problem, WO 2009/007718 A1 as well as the German Utility Model DE 20 2018 107 052 have already disclosed a protective device for the needle tube of a syringe. In this known protective device from the prior art, the needle tube of the syringe is located on a support base which is accommodated by it. The outlet of the syringe is attached to the support base or the needle tube. In this manner, the protective device is then connected to the body of the syringe. In this regard, for protection, a pivotably mounted housing is disposed on the support base which in particular has an open housing side, in particular at its pivot plane. When the syringe is used in order to carry out an injection, the housing which is pivotably mounted on the support base is pivoted out of the way so that the needle tube is free and an injection can then be made. After the injection, the housing is pivoted back, whereupon the needle tube pivots back into the housing through the open housing side so that after being used for injection, the needle tube is once again located in the housing. So that inadvertent pivoting of the housing portion on the support base is prevented following use, according to the prior art, retaining device in the form of clamps or catches are provided on the housing walls of the pivotable housing which grip the needle tube and thus prevent inadvertent pivoting of the needle tube out of the housing.

A disadvantage which is observed this known protective device of the prior art is that with the known embodiments, what is known as an unintentional pivoting process could occur so that then—without an injection having taken place—this exposes the needle tube. Furthermore, the fact that the retaining device cannot guarantee secure retention after being used for injection, because the housing has swung back, is also seen as a disadvantage.

Another problem is that even when the syringe has not been used, problems may arise because an unintentional pivoting process has commenced, which then exposes the needle tube and it is unprotected. In this regard, the syringes are stored one beside the other in the packaging. If one or more syringes are then removed from this packaging, the problem arises that the needle can jump out of the housing which is covered with a film because the outer packaging has been opened incorrectly. In addition, the problem arises that the known retaining devices here do not hold the needle tube in the desired protected position in the housing, whereupon the needle tube can jump out of the housing at any time upon improper removal. The result is that there is no indication that the retaining device in particular is securely retaining the needle in the housing.

Furthermore, the fact that the known embodiments of protective devices are very expensive as regards their manufacturing costs is also seen as a disadvantage; in this regard too, the fact that cheap manufacture often means that important requirements regarding details are overlooked because they affect the manufacturing cost structure must also be taken into account.

BRIEF SUMMARY OF THE INVENTION

Thus, the problem to be solved by the invention is to further develop a protective device for a needle tube of a syringe which in particular overcomes the aforementioned disadvantages, wherein the protective device is substantially modified in a manner such that it is substantially more hygienically designed for what is known as the park station, with the proviso that in particular, the manufacturing costs can be substantially reduced.

The object is achieved by a protective device for a needle tube of a syringe, the protective device including a support base that supports the needle tube; a housing pivotably connected at the support base and including an open housing side in a pivot plane, so that the needle tube is pivotable into the housing after being used for an injection, wherein the housing is connected at the support base by a film hinge that forms a pivot axis and by a predetermined breaking point; a retaining device arranged at the housing and configured to engage the needle tube pivoted into the housing after being used for injection, wherein the housing is pivotable back over the destroyed predetermined breaking point into a latched position where the needle tube is engaged by the retaining device arranged in the housing.

The advantages obtained by the invention consist in the fact that because of the inexpensive manufacture of a monobloc protective device for the needle tube of a syringe, all of the requirements for safe handling of the item are met. In this regard, it is ensured that unintentional flipping open of the housing region prior to injection is prohibited because this is prevented by a predetermined breaking point which is injection moulded in this case. Furthermore, the retaining devices in accordance with the invention ensure that the needle tube is prevented from coming loose from the housing which has been pivoted back.

Thus, in accordance with the invention, it is proposed that, in addition to the connection of a film hinge in order to form a pivot axis, the support base and the pivotable housing are additionally connected together via a predetermined breaking point and wherein after being used for injection, the housing can be pivoted back over the destroyed predetermined breaking point. Because of this construction, by means of the monobloc configuration of the protective device, in this case, prior to use, the support base is firmly connected to the pivotable housing, wherein the pivotability is not compromised because here what is known as the predetermined breaking point means that the predetermined breaking point can be torn open by the application of manual pressure, so that pivoting can then be carried out. In particular, in this case, the predetermined breaking point prevents what is known as swing-out upon removal from packaging. In addition, after the predetermined breaking point has been destroyed, the protective device is still in a condition wherein it can still accommodate the needle in the pivotable housing after injection because on the one hand, because the housing swings back, the retaining device engages in the housing, wherein on the other hand, overswinging of the housing then means that the needle tube cooperates with the interior latch so that the retaining device ensures that the needle tube is accommodated in the pivotable housing following injection.

In a variation of the invention, the predetermined breaking point consists of injection moulded flexible web elements. In this regard, the web elements are disposed on and connected to the edge portions of support base and housing edge, wherein they are injection moulded in a distributed manner over the edge portion of the support base and housing.

In accordance with an advantageous embodiment, after being used for injection, the housing can be pivoted back over the predetermined breaking point into a latched position, wherein the needle tube can be brought into operational connection with a retaining device provided in the housing. In this embodiment, the housing is pivoted over a pivot point so that in the latched end position, the support base and housing are in a slightly inclined position with respect to each other. This has the particular advantage that the inclined position ensures that the retaining device engages into the housing for the needle tube.

In accordance with the invention, a retaining device is proposed in this regard which consists of two tongues formed in the housing on the housing wall, which are orientated in the manner of a harpoon in the direction in which the needle tube pivots inwards. In order to forcibly guide the needle as it pivots inwards, so that the needle either jumps behind one or behind the other of the tongues, a peg element with a triangular configuration is provided between the tongues which forces the needle tube which has pivoted inwards under one or the other tongue.

In a further variation of the protective device as an injection moulded monobloc component, the retaining device here consists of a deformable sleeve which is connected to the housing via sawtooth-like predetermined breaking points. The predetermined breaking points are formed on the housing front by means of protruding web struts, wherein the web struts are formed on the outside of the housing wall. Because of this construction, in this case, a retaining device in the form of a deformable sleeve is provided which can be injection moulded directly along with the housing part; here again, this means that the manufacturing costs are substantially reduced.

In this regard, it should be noted that the protective device is produced as a monobloc from an injection moulded part with support bases, needle housing, predetermined breaking point as well as the retaining device.

In accordance with an advantageous variation of the invention, optionally, a protective sleeve may cooperate with the housing which is pivotably mounted on the support base, by means of which, after being used for injection, the open housing side located in the pivot plane can be closed. The protective sleeve means that the protective device in which the needle tube is clamped and interlocked can additionally be hermetically sealed. In this regard, the protective sleeve has an opening disposed in the wall which is congruent with the open side located on the housing. This means that the protective sleeve does not impede the needle when it pivots outwards, because the retained needle can pivot through the opening of the protective sleeve. The protective sleeve is rotatably mounted on the housing so that after being used for injection, it can be turned from an open position into a position which closes the housing.

In this regard, the protective sleeve is connected and rotatably mounted with its lower housing edge on the edge portion of the housing by interlocking. In order to prohibit unintentional twisting of the protective sleeve on the housing after being used for injection, a catch is formed on the edge portion of the housing which, after twisting the protective sleeve through 180° on the housing, cooperates with an aperture disposed in the wall of the protective sleeve which produces the latched position of the protective sleeve on the housing. The upper cover portion of the protective sleeve comprises a grip on the underside of which a ring element is formed and which cooperates with a shaped 180° control cam which cooperates with a wedge formed on the cover portion of the housing, which prevents the protective sleeve from turning backwards after interlocking the control cam with the wedge.

In accordance with a particularly advantageous variation, the upper cover portion of the protective sleeve has a grip. A ring element is formed on the underside of the grip, wherein a control cam which is curved around 180° is shaped into the ring element. The formed control cam cooperates in this regard with a wedge formed on the cover portion of the housing which locks into the end region of the curve when it traverses the control cam. In this manner, twisting of the protective sleeve backwards after interlocking the control cam with the wedge is prohibited. In order to fix the grip on the protective sleeve, the ring element has a circular aperture located in the axis of rotation through which a locking clamp reaches and engages with the covering region of the housing.

BRIEF DESCRIPTION OF THE DRAWINGS

The invention will now be described in more detail with reference to an exemplary embodiment which is shown in the figures, in which.

DETAILED DESCRIPTION OF THE INVENTION

Figure 1:
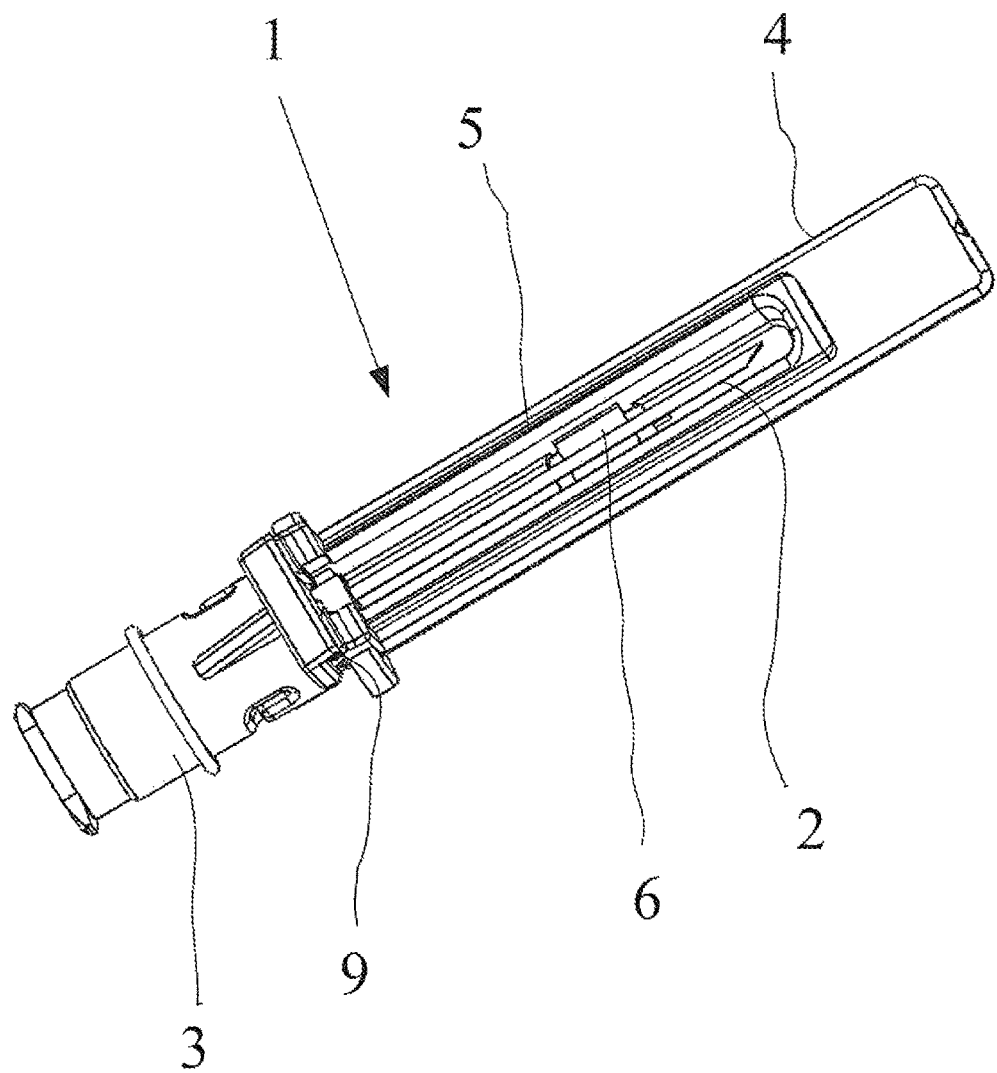
FIG. 1 shows a perspective view of a protective device in accordance with a first embodiment.
Figure 2:
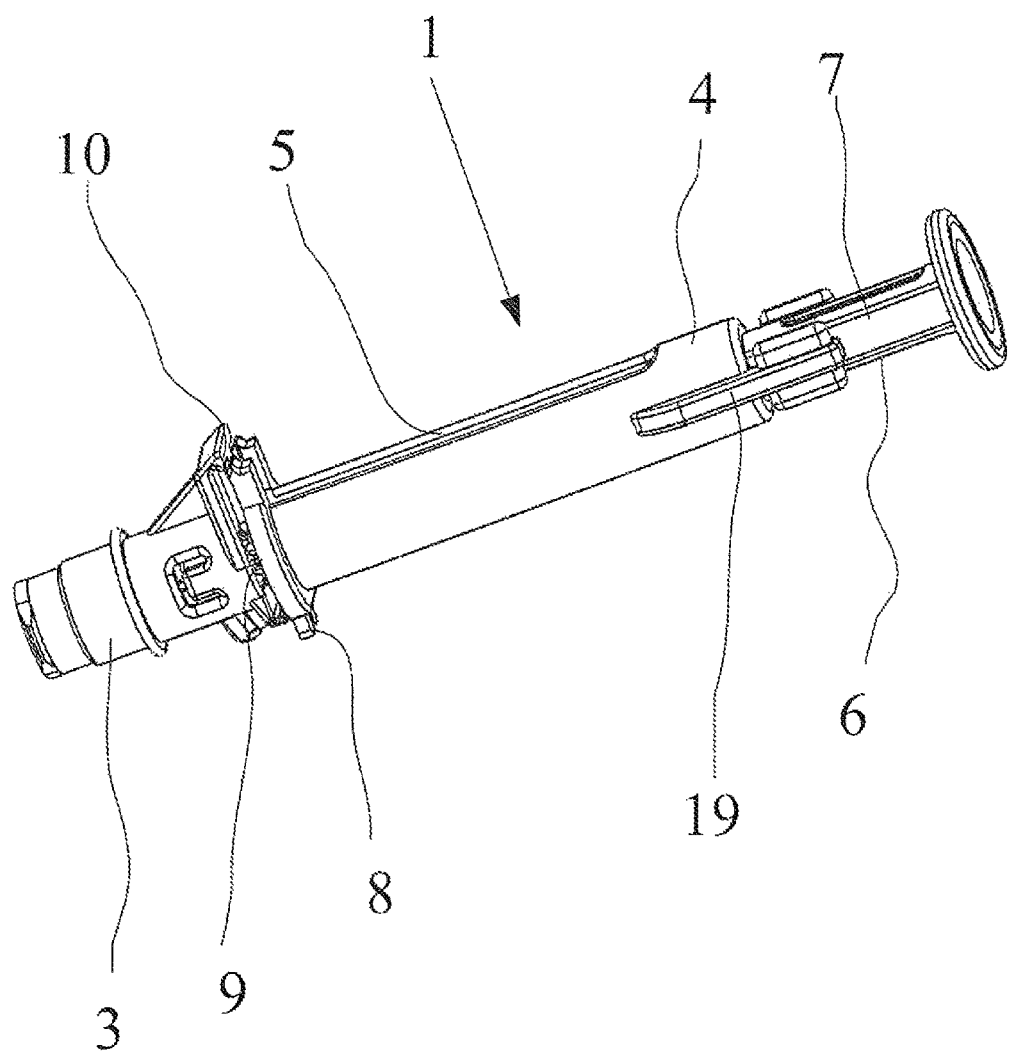
FIG. 2 shows a further perspective view in accordance with a further embodiment.

FIGS. 1 and 2 respectively show, in perspective views, a protective device 1 for a needle tube 2 of a syringe, not shown in any further detail, in two different exemplary embodiments. In this regard, the protective device 1 comprises a housing 4 for the needle tube 2 which is constructed to as to be pivotable on a support base 3 and which has an open housing side 5 in the pivot plane of the housing 4. Because of the open housing side 5, it is possible for the needle tube 2 to be pivoted into the housing 4 after being used for injection, so that it is then protected.

In particular, in order to protect the needle tube 2 from improper use after the injection, on the housing side, a retaining device 6 is provided for the needle tube 2 which has been pivoted inwards, wherein FIG. 1 shows a retaining device 6 inside the housing 4, which here is configured as a clamping means, whereas FIG. 2 shows the retaining device 6 which covers the needle tube 2 with a sleeve 7 in order to protect it.

Figure 3:
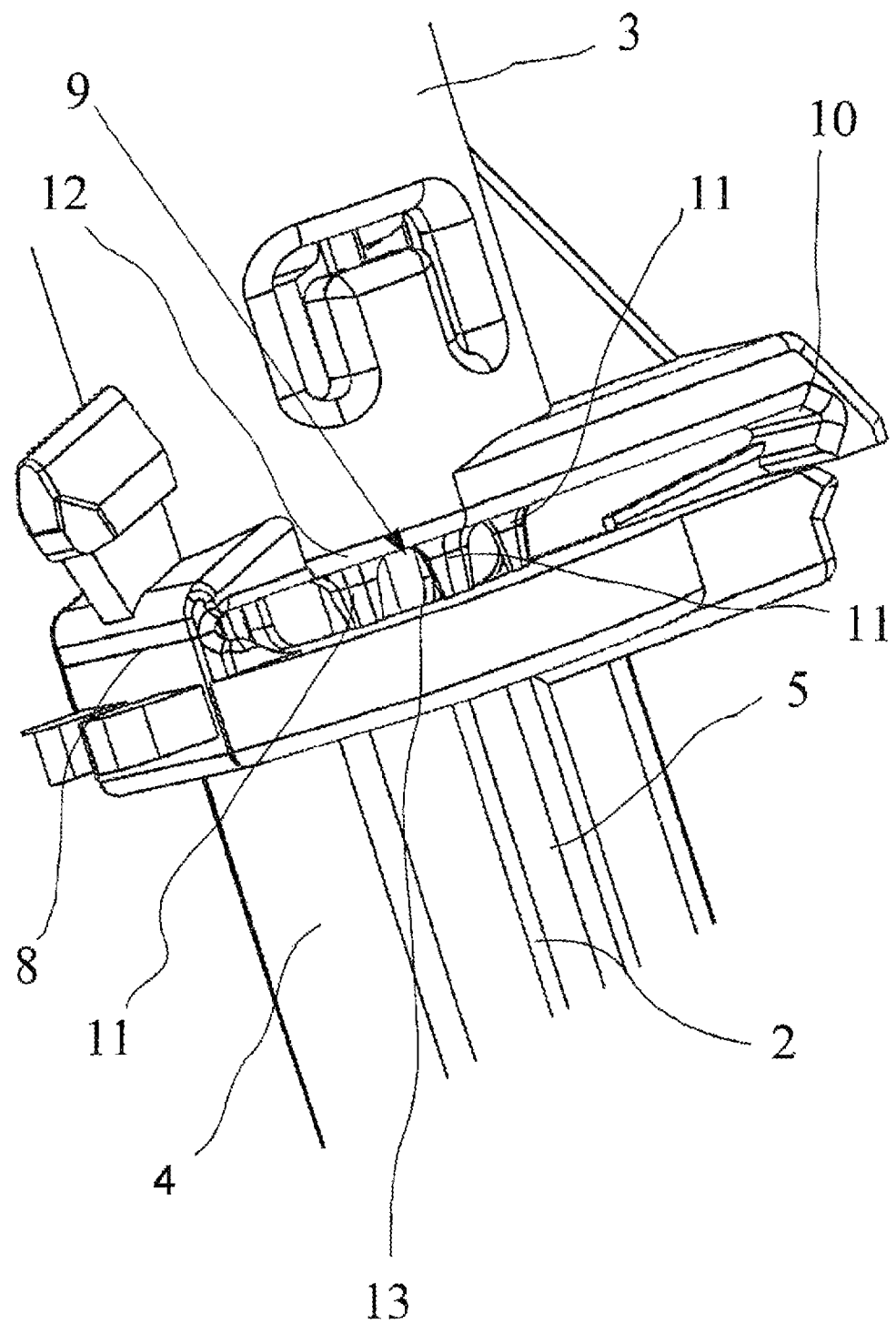
FIG. 3 shows a detailed view, in particular of the predetermined breaking point of the invention between the support base and pivotable housing.
Figure 4:
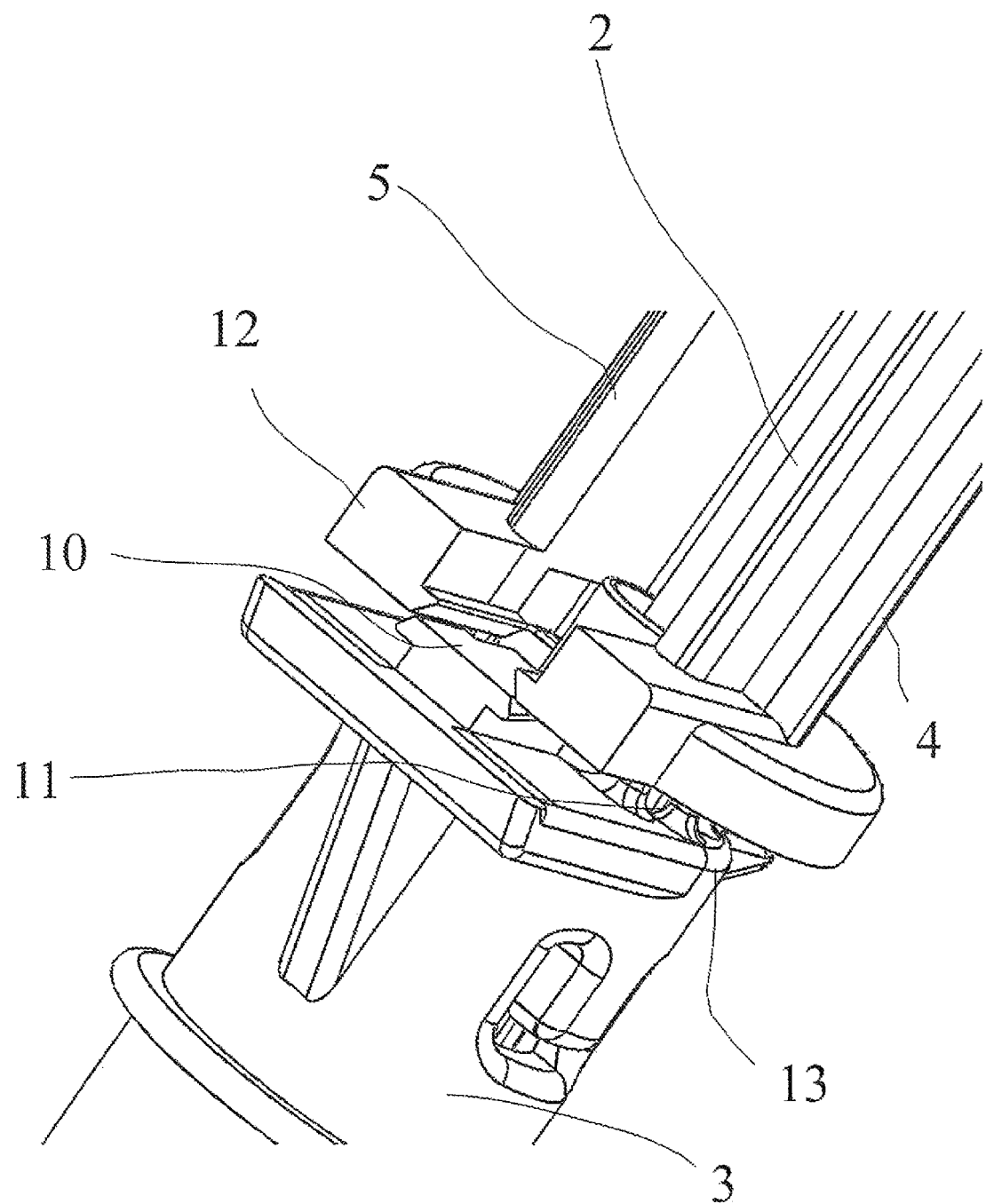
FIG. 4 shows a further perspective view in accordance with FIG. 3, in another view.
Figure 5:
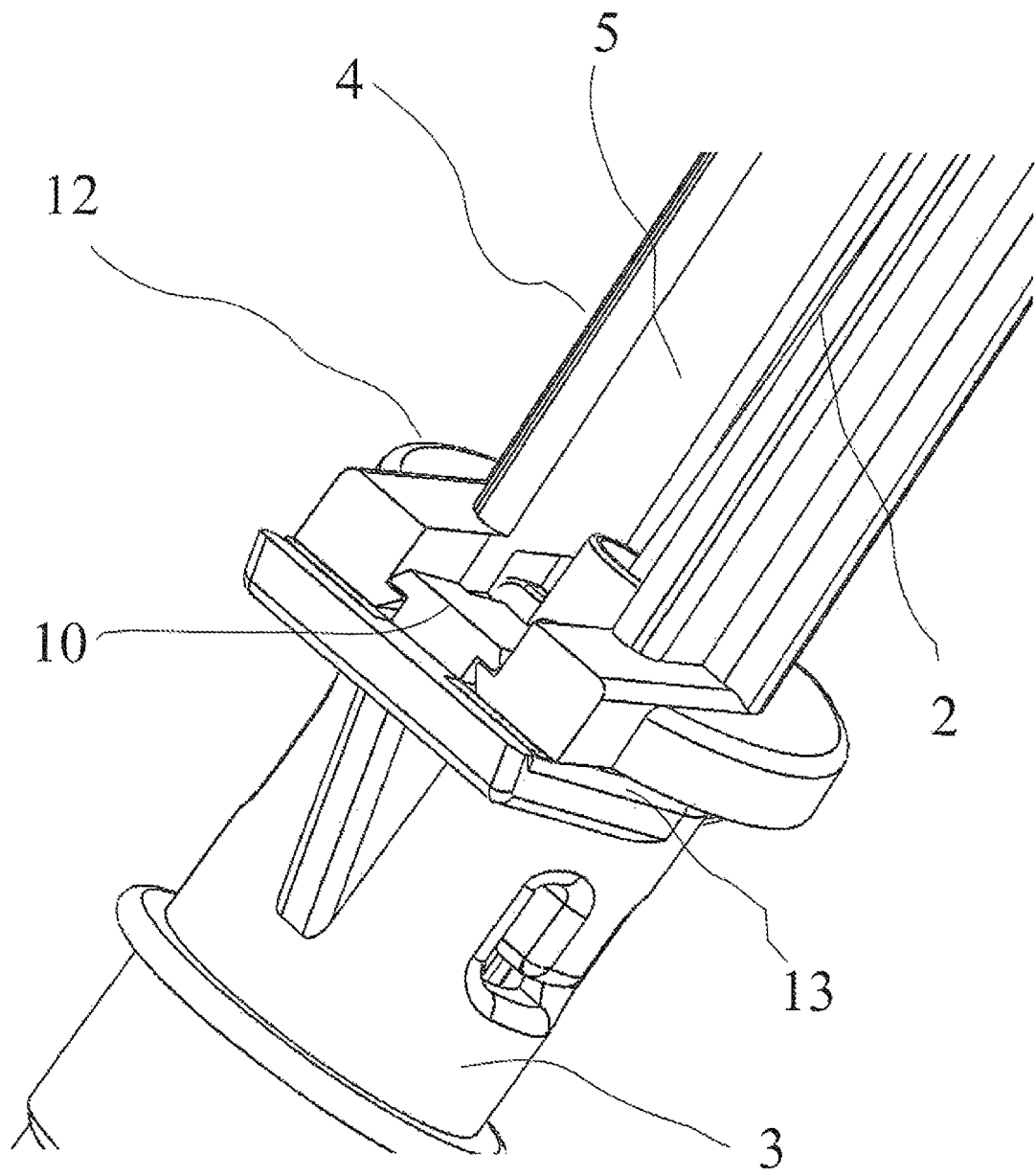
FIG. 5 shows a further view in accordance with FIGS. 3 and 4 in the latched condition in the inclined position of the housing with respect to the support base.
Figure 7:
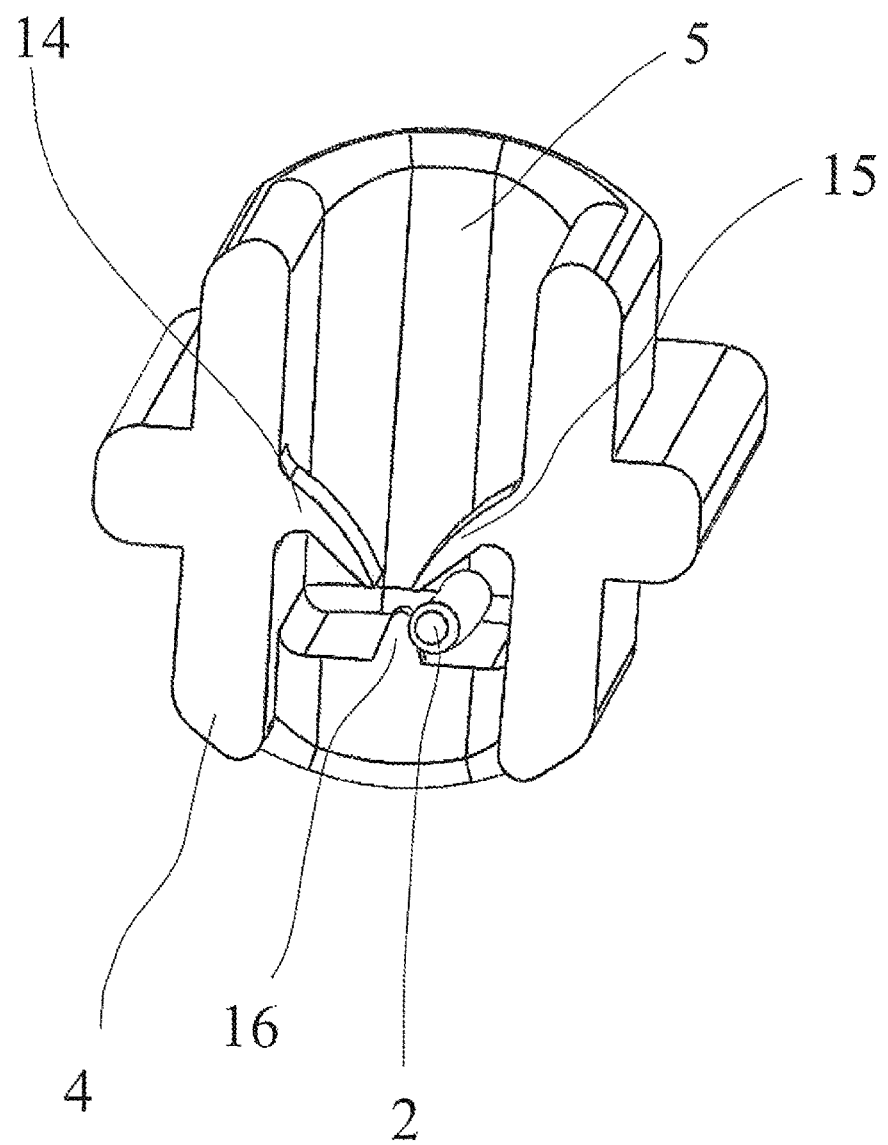
FIG. 7 shows a further view of the retaining device in a detailed view in accordance with FIG. 6 in what is known as the latched position.

In the protective device 1 in accordance with the invention, as can be seen in more detail in FIGS. 3 and 4, in addition to being connected by a film hinge 8, the support base 3 and the pivotable housing 4 are also connected via a predetermined breaking point 9 via which the support base 3 and the housing 4 are connected in order to form a pivot axis. If the predetermined breaking point 9 is destroyed, in the embodiment in accordance with the invention, it is possible for the housing 4 to be pivoted back over the destroyed predetermined breaking point 9 after being used for injection, as can be seen in FIG. 5, whereupon then, a catch 10, shown in FIG. 5, is operated. In this position of FIG. 5, the housing 4 is in a slightly inclined position with respect to the support base 3, so that in particular the retaining device 6 as can be seen in FIG. 7, is also operated. In this position, the housing 4 is in the latched position, such that it assumes a slightly inclined position over the film hinge 8, whereupon latching of the catch 10 occurs.

As can be seen in more detail in FIGS. 3 and 4 in particular, the predetermined breaking point 9 consists of injection moulded flexible web elements 11 which are disposed on the edge portions 12 and 13 of the support base 3 and housing 4. In this regard, the web elements 11 are distributed over the edge portions 12 and 13, as can be seen when FIGS. 3 and 4 are viewed together, and as also can be seen in FIG. 2. As already indicated, after being used for injection, the housing 4 can be pivoted back over the predetermined breaking point 9 into a latched position, shown in FIGS. 4 and 5, wherein the needle tube 2 can be brought into operative connection with a retaining device 6 provided in the housing 4.

Figure 6:
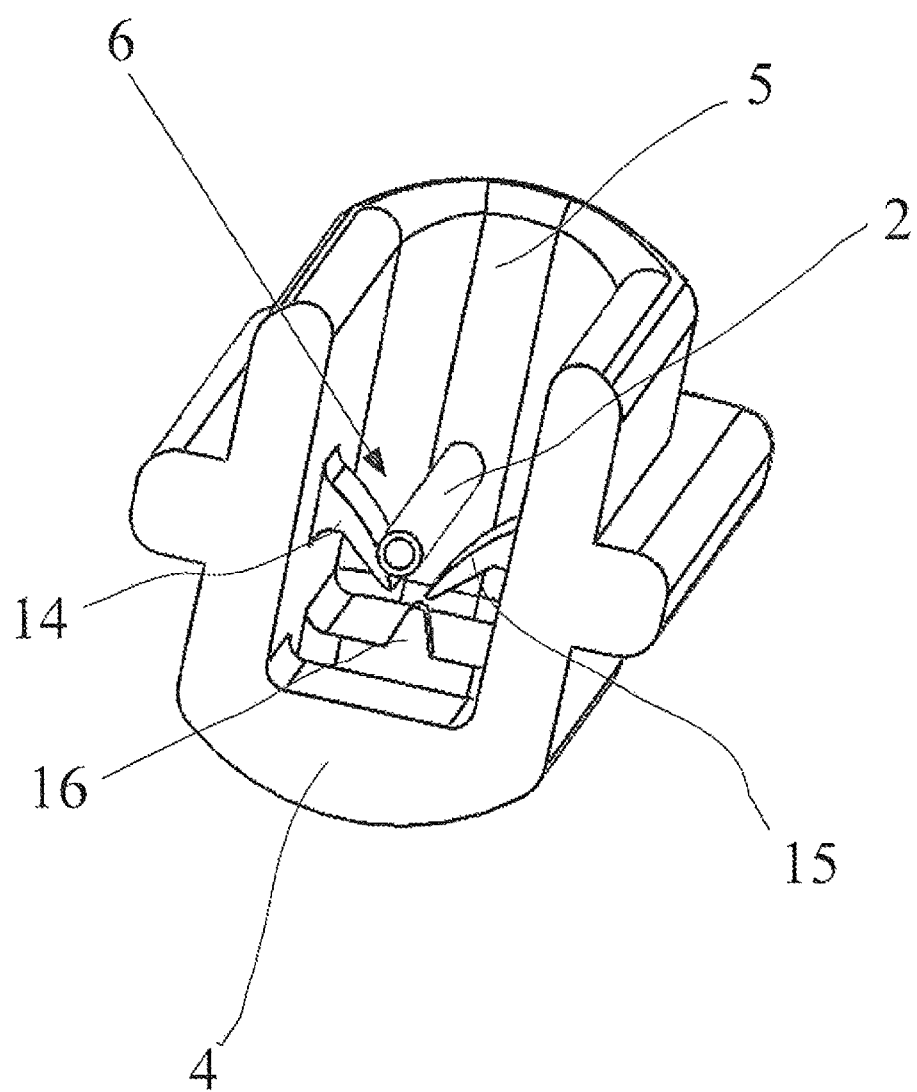
FIG. 6 shows a detailed view of the retaining device of a first embodiment.
Figure 8:
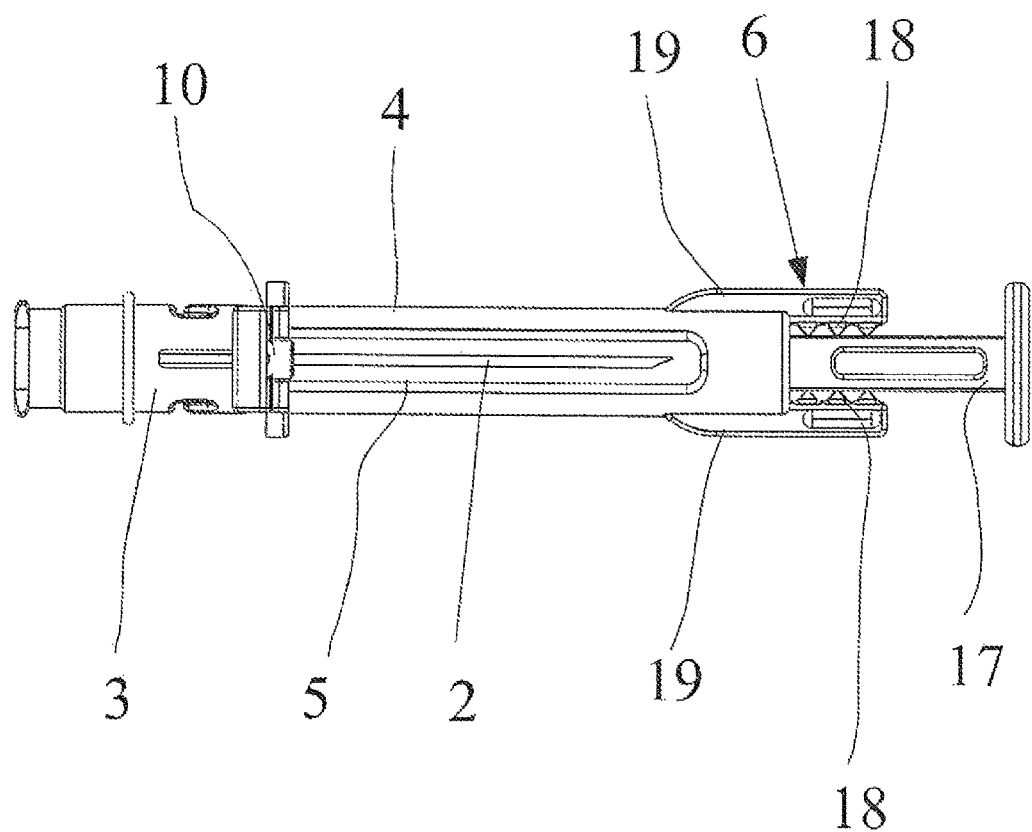
FIG. 8 shows a further side view of the retaining device in accordance with the second embodiment, and in fact in accordance with FIG. 2.

The different retaining device 6 are shown in more detail here in FIGS. 6 and 7 as well as in FIGS. 1 and 8. In this regard, FIGS. 6 and 7 in combination with FIG. 1 show a retaining device 6 which consists of two tongues 14 and 15 formed on the housing wall in the housing 4, as can be seen in particular in more detail in FIGS. 6 and 7. In this regard, the tongues 14 and 15 are configured in the manner of a harpoon such that they engage behind the needle tube 2 in the inward-pivoting direction of the needle tube 2 after it has passed through. In order to promote the engagement process, between the tongues 14 and 15, a peg element 16 formed in the shape of a triangle is provided which pushes the needle tube 2 which has been pivoted inwards below one tongue 14 or the other tongue 15. It is clear that when the needle tube 2 pivots inwards and what is known as the latched position in accordance with FIG. 5 is produced, the position of the needle tube 2 as shown in FIG. 7 is assumed, wherein when the needle tube 2 pivots inwards, it is pushed either to the left or to the right and thus goes into the stable position of being retained.

In accordance with a further embodiment concerning the retaining device 6, in particular as shown in FIG. 8 in combination with FIG. 2, the retaining device 6 consists of a sleeve 17 which can be deformed, which is connected to the housing 4 via sawtooth-like predetermined breaking points 18. As can be seen, the predetermined breaking points 18 are formed onto the housing side with protruding web struts 19. The web struts 19 in this regard are formed on the outside on the housing wall, as can be seen particularly well in FIG. 2, but can also be seen in the sectional view of FIG. 8. In both embodiments of the retaining device 6, the following applies, wherein in particular, these retaining device, as described and also shown in FIGS. 6, 7 but also 8, are all injection moulded together in a single injection moulding process so that in addition to the housing 4 and the support base 3, the retaining device 6 is also co-injection moulded and shaped.

This is also the case for the entire protective device 1, which here can be injection moulded as a monobloc part in a manner such that, in addition to the predetermined breaking points 9, 18, the film hinge 8, the catch 10 as well as the two different retaining device 6 can be injection moulded in a single operation or in a single tool.

Figure 9:
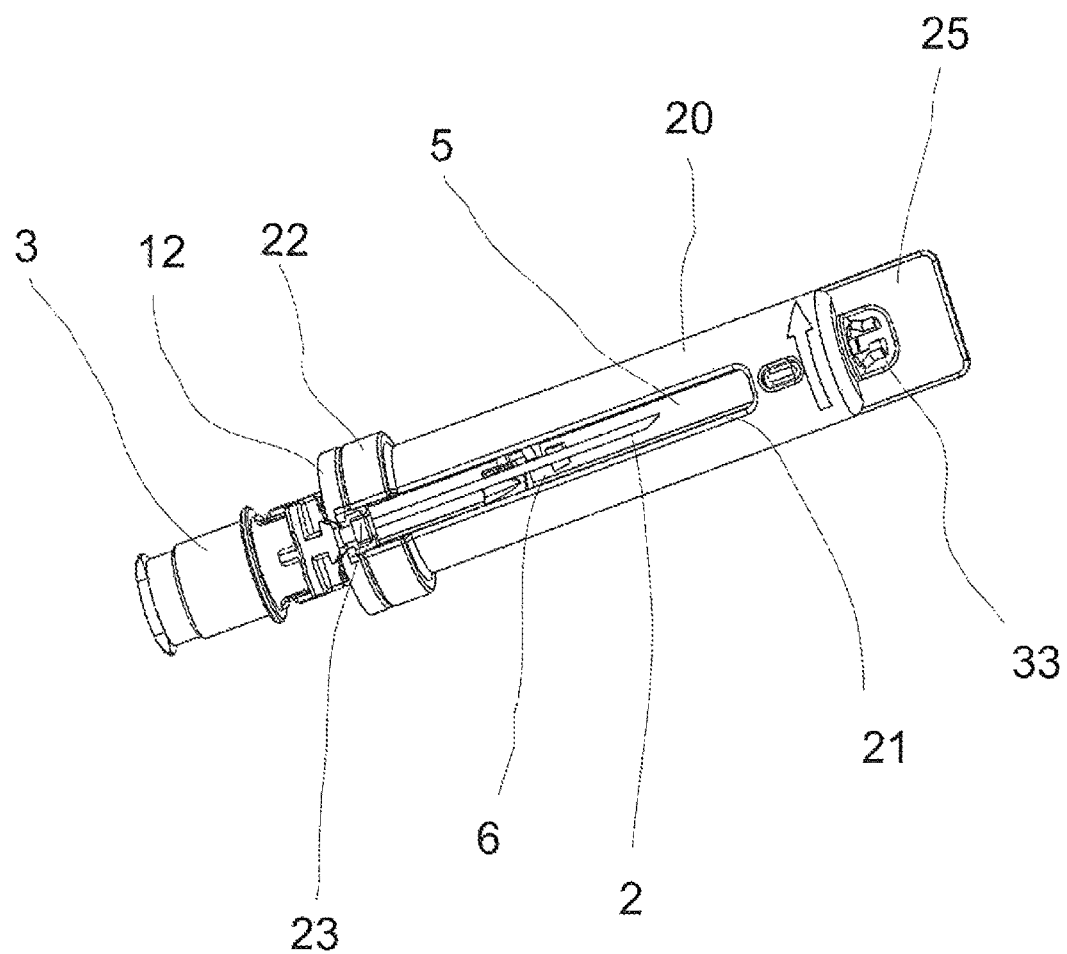
FIG. 9 shows a perspective view of the protective device with the protective sleeve in the open position.
Figure 10:
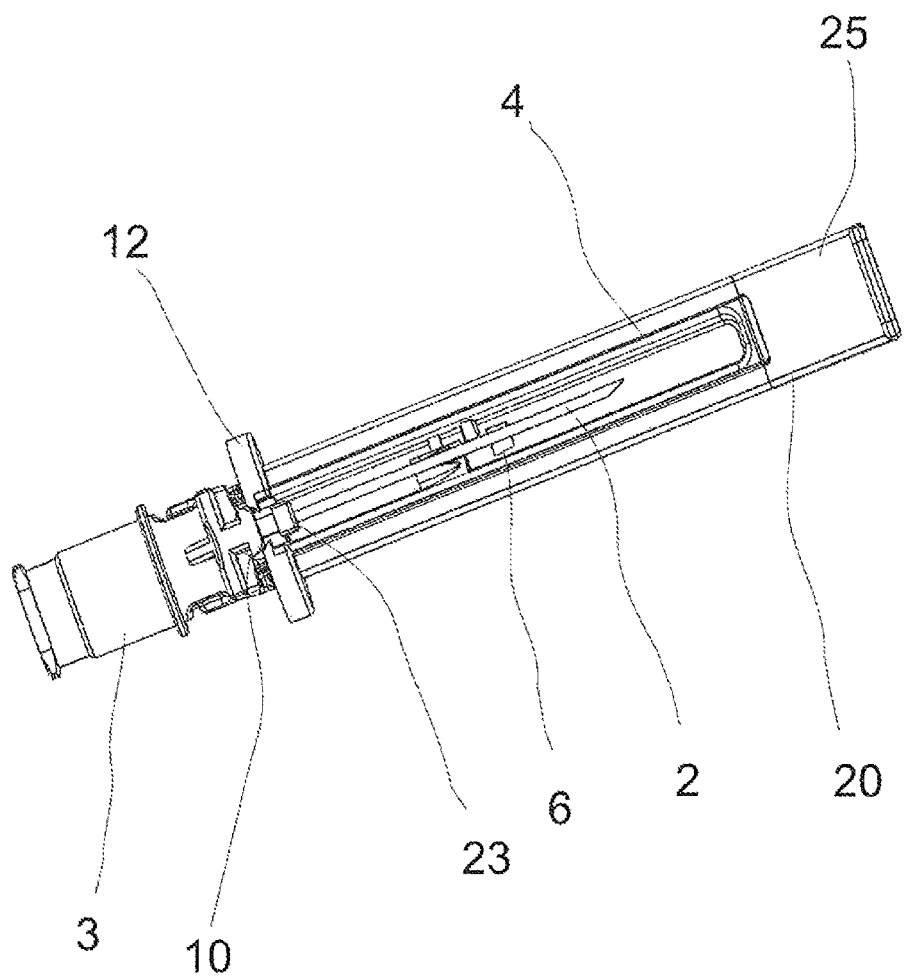
FIG. 10 shows a partial sectional front view in accordance with FIG. 9.
Figure 11:
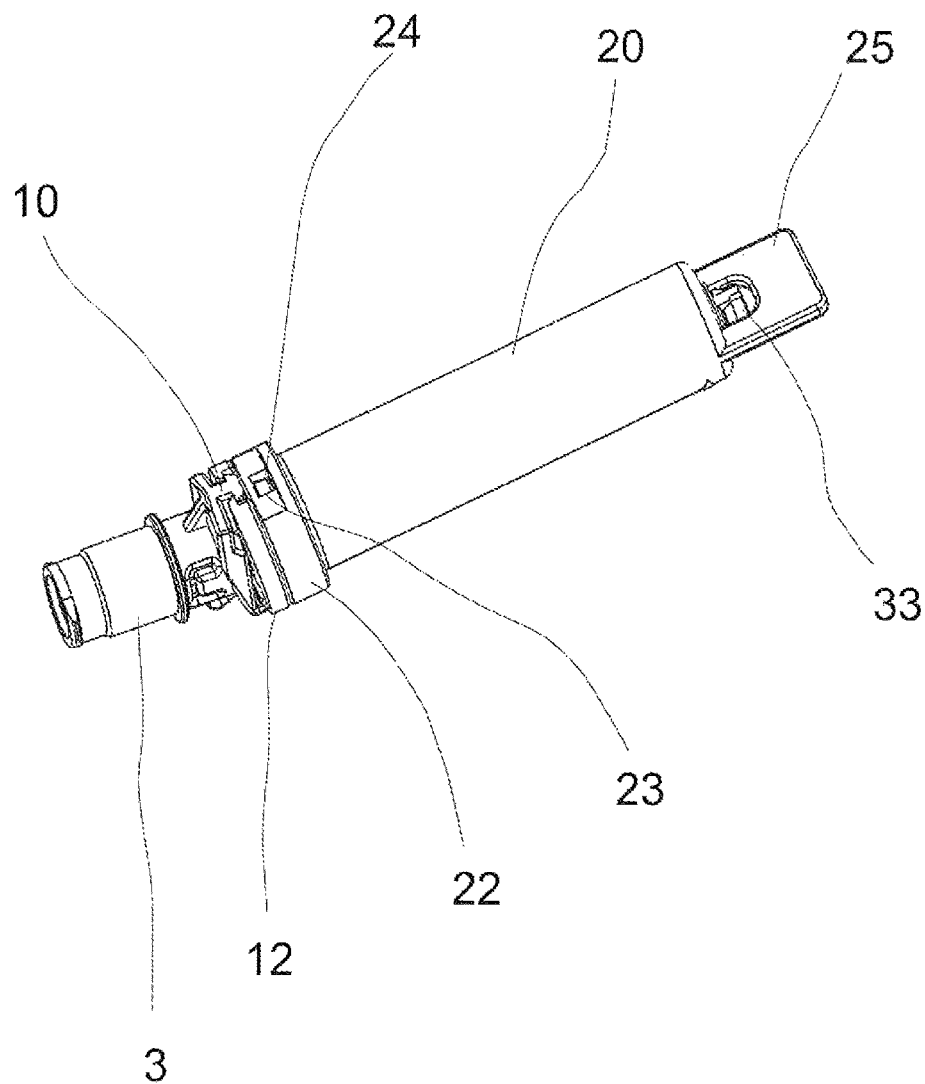
FIG. 11 shows a further perspective view of the protective device with the protective sleeve in the closed position.

In accordance with an advantageous variation of the invention, shown in FIGS. 9, 10 and 11, a protective sleeve 19 can optionally cooperate with the housing 4 pivotably mounted on the support base 3, by means of which protective sheath, after being used for injection, the open housing side 5 located in the pivot plane can be closed. The protective sleeve 19 enables the protective device 1 in which the needle tube 2 is clamped and interlocked to be hermetically sealed in addition. To this end, the protective sleeve 20 has an opening 21 disposed in the wall which is congruent with the open side 5 of the housing. In this manner, the protective sleeve 20 does not prevent the needle tube 2 from pivoting outwards, because the retained needle tube 2 can pivot through the opening 21 of the protective sleeve 20. The protective sleeve 20 is rotatably mounted on the housing 4 so that it can be turned from an open position after being used for injection, shown in FIG. 9, into a position which closes the housing 4, as shown in FIG. 11.

In this regard, the lower housing edge 22 of the protective sheath 20 is rotatably mounted on and interlocked with the housing 4. The interlocking here may, for example, be obtained by means of a snap fit connection. In order to prevent unintentional twisting of the protective sleeve 20 on the housing 4 after being used for injection, a catch 23 is formed at the edge portion 12 of the housing 4 which, after twisting the protective sleeve 20 through 180°, shown in FIG. 11, cooperates on the housing 4 with an aperture 24 disposed in the wall of the protective sleeve 20, which generates the latched position of the protective sleeve 20 on the housing 4.

Figure 12:
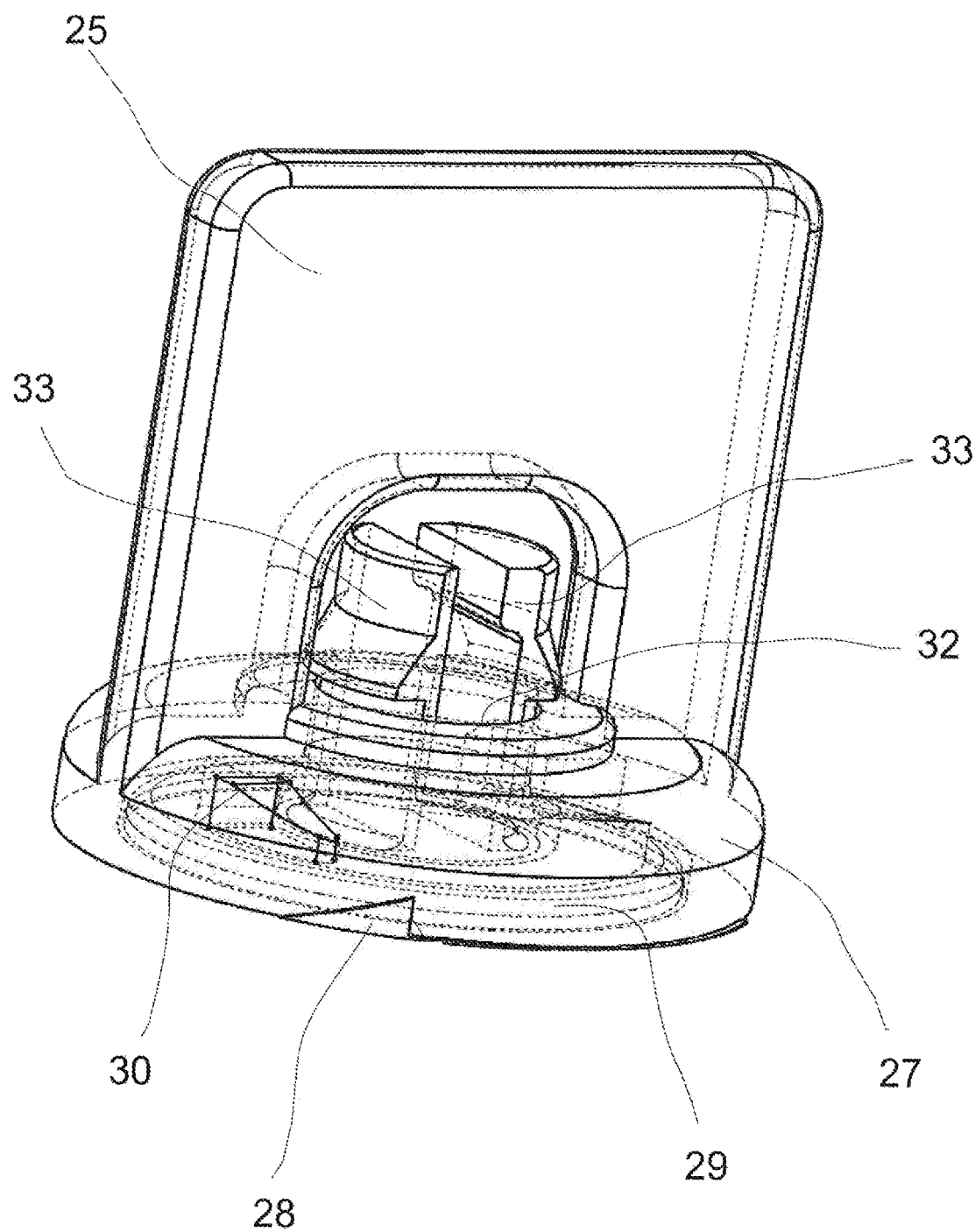
FIG. 12 shows a perspective view of a grip for the protective sleeve in operational connection with the housing, shown in dashed lines.
Figure 13:
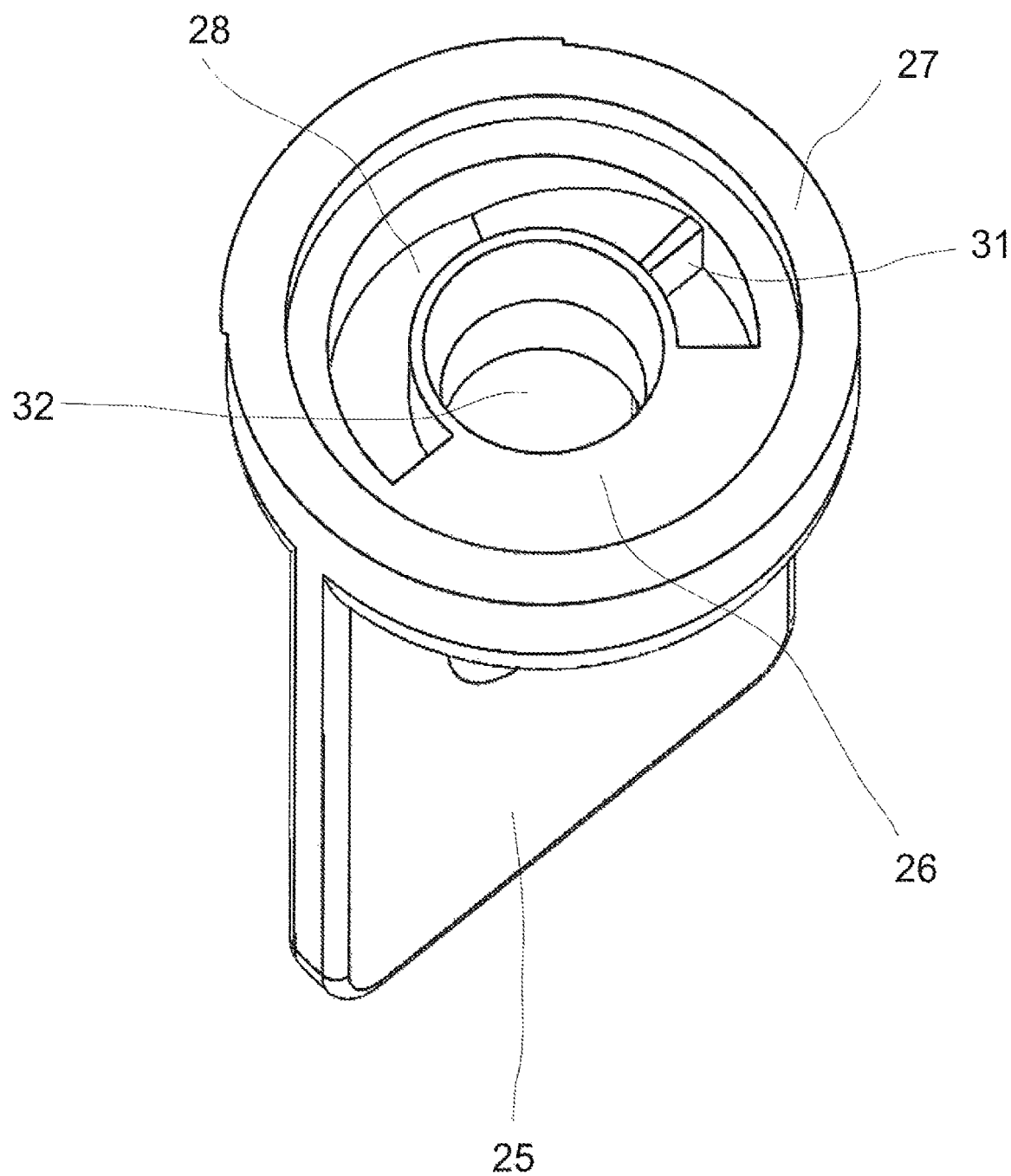
FIG. 13 shows a further perspective view of the grip, in a bottom view.

In accordance with a particularly advantageous variation, shown in FIGS. 12 and 13, the protective sleeve 20 has a grip 25 at its upper cover portion. A ring element 27 is formed on the underside 26 of the grip 25, wherein a 180° curved control cam 28 is formed in the ring element 27. The formed control cam 28 in this regard cooperates with a wedge 30 formed on the cover portion 29 of the housing 4 which locks in the end region of the curve at the step 31 when it traverses the control curve 28. In this manner, twisting the protective sleeve 20 backwards after locking the control cam 28 with the wedge 30 is prohibited.

In order to fix the grip 25 on the protective sleeve 20, the ring element 27 has a circular aperture 32 located in the axis of rotation through which the locking tongues 33 which are formed on the cover portion of the housing 4 reach. In the inserted condition of the grip 25, the locking tongues 33 then interlock on the edge of the circular aperture 32, whereupon correspondingly, as described, the control cam 28 comes into operative connection with the wedge 30.

REFERENCE NUMERALS AND DESIGNATIONS

1 protective device
2 needle tube
3 support base
4 housing
5 open housing side
6 retaining device
7 sleeve
8 film hinge
9 predetermined breaking point
10 catch
11 web elements
12 edge portion
13 edge portion
14 tongue
15 tongue
16 peg element
17 sleeve
18 sawtooth predetermined breaking point
19 web struts
20 protective sleeve
21 opening in wall of protective sleeve
22 housing edge under protective sleeve
23 catch
24 aperture
25 grip
26 grip, underside
27 ring element
28 control cam
29 cover portion of housing
30 wedge
31 step
32 ring element aperture
33 locking tongues

What is claimed is:

1. A protective device for a needle tube of a syringe, the protective device comprising:
   a support base that supports the needle tube;
   a housing pivotably connected at the support base and including an open housing side in a pivot plane, so that the needle tube is pivotable into the housing after being used for an injection,
   wherein the housing is integrally molded in one piece with the support base and connected at the support base by a film hinge that forms a pivot axis and by en integrally molded predetermined breaking point so that the housing is in a non-inclined position relative to the support base and the needle tube, wherein the integrally molded predetermined breaking point is broken by pivoting the housing about the pivot axis out of the non-inclined position relative to the support base and away from the support base;
   a self-acting retaining device arranged at the housing and configured to not engage the needle tube when the housing is in the non-inclined position relative to the support base and the needle tube and configured to directly engage the needle tube pivoted into the housing self-acting by positive form locking in an inclined position of the housing relative to the support base and the needle tube after being used for the injection;
   a self-acting catch arranged at the support base and configured to engage the housing self-acting in a latched position in the inclined position of the housing relative to the support base and the needle tube,
   wherein the housing is pivotable back over the integrally molded predetermined breaking point after being broken so that the housing is pivoted into the latched position where the needle tube is engaged by the self-acting retaining device self-acting,
   wherein the self-acting catch engages the housing self-acting when the housing is pivoted into the latched position,
   wherein the housing pivots back towards the support base over the predetermined breaking point beyond the non-inclined position into the inclined position relative to the support base when the self-acting catch engages the housing self-acting and the self-acting retaining device simultaneously engages the needle tube self-acting in the inclined position of the housing relative to the support base and the needle tube
   wherein the self-acting catch and the film hinge are arranged on radially opposite sides of an axis of the needle tube and a radial distance of the self-acting catch from the axis of the needle tube is greater than a radial distance of the integrally molded predetermined breaking point from the axis of the needle tube and a distance of the self acting catch from the film hinge is greater than a distance of the integrally molded predetermined breaking point from the film hinge in the inclined position of the housing relative to the support base and the needle tube when the integrally molded predetermined breaking point is broken and the housing is engaged by the self-acting catch and the needle tube is engaged by the self-acting retaining device.

2. The protective device according to claim 1, wherein the integrally molded predetermined breaking point includes injection molded flexible webs.

3. The protective device according to claim 2, wherein the injection molded flexible webs are arranged at an edge portion of the support base and an edge portion of the housing.

4. The protective device according to claim 3, wherein the injection molded webs are distributed over the edge portion of the support base and the edge portion of the housing.

5. The protective device according to claim 1, wherein the retaining device includes of two hooks formed in the housing at a housing wall, which are oriented in a direction in which the needle tube pivots into the housing.

6. A protective device for a needle tube of a syringe, the protective device comprising:
a support base that supports the needle tube;
a housing pivotably connected at the support base and including an open housing side in a pivot plane, so that the needle tube is pivotable into the housing after being used for an injection,
wherein the housing is connected at the support base by a film hinge that forms a pivot axis and by a predetermined breaking point;
a retaining device arranged at the housing and configured to engage the needle tube pivoted into the housing after being used for injection,
wherein the housing is pivotable back over the predetermined breaking point after being broken so that the housing is pivoted into, a latched position where the needle tube is engaged by the retaining device,
wherein the retaining device includes of two hooks formed in the housing at a housing wall, which are oriented in a direction in which the needle tube pivots into the housing;
a peg with a triangular configuration arranged between the hooks,
wherein the peg forces the needle tube which has been pivoted inwards under one or the other of the hooks.

7. The protective device according to claim 6, wherein the retaining device includes a deformable sleeve connected to the housing by sawtooth shaped predetermined breaking points.

8. The protective device according to claim 7, wherein the sawtooth shaped predetermined breaking points are formed at protruding web struts at a housing face.

9. The protective device according claim 8, wherein the protruding web struts are formed at, a housing wall.

10. The protective device according to claim 9, wherein the protective device is produced integrally in one piece as an injection moulded part including the support base, the housing, the predetermined breaking point, and the retaining device.

11. A protective device for a needle tube of a syringe, the protective device comprising:
a support base that supports the needle tube;
a housing pivotably connected at the support base and including an open housing side in a pivot plane, so that the needle tube is pivotable into the housing after being used for an injection,
wherein the housing is connected at the support base by a film hinge that forms a pivot axis and by a predetermined breaking point;
a retaining device arranged at the housing and configured to engage the needle tube pivoted into the housing after being used for injection,
wherein the housing is pivotable back over the predetermined breaking point after being broken so that the housing is pivoted into a latched position where the needle tube is engaged by the retaining device;
a protective sleeve that cooperates with the housing and is rotatably mounted on the support base so that the open housing side located in the pivot plane is closable by the protective sleeve.

12. The protective device according to claim 11, wherein the protective sleeve includes an opening in a wall which is congruent with the open housing side.

13. The protective device according to claim 11, wherein the protective sleeve is rotatably mounted on the housing so that the protective sleeve is rotatable from an open position into a position which closes the housing after being used for the injection.

14. The protective device according to claim 11,
wherein the protective sleeve is rotatably mounted with a lower sleeve edge on an edge portion of the housing,
wherein a catch is formed on the edge portion of the housing, and
wherein the catch engages an aperture formed in a wall of the protective sleeve after rotating the protective sleeve by 180° on the housing.

15. The protective device according to claim 14,
wherein an upper cover portion of the protective sleeve includes a grip,
wherein a bottom side of the grip forms a ring collar including a shaped 180° control cam which cooperates with a wedge formed on a face portion of the housing which prevents the protective sleeve from turning backwards after the control cam has interlocked with the wedge.

16. The protective device according to claim 15, wherein the grip is fixable to the face portion of the housing by locking tongues which reach through the ring collar.

17. The protective device according to claim 1, wherein the housing is pivotable back over the integrally molded predetermined breaking point, after being broken so that the housing is pivoted into the latched position where the needle tube is engaged by the self-acting retaining device self-acting while the integrally molded predetermined breaking point is compressed after being broken.

* * * * *